United States Patent [19]

Lin et al.

[11] Patent Number: 4,519,956

[45] Date of Patent: May 28, 1985

[54] PROCESS FOR SELECTIVELY PREPARING ACETIC ANHYDRIDE BY CARBONYLATION OF METHYL ACETATE IN THE PRESENCE OF AN IODIDE-FREE CATALYST SYSTEM

[75] Inventors: Jiang-Jen Lin, Round Rock; Roger G. Duranleau, Georgetown, both of Tex.

[73] Assignee: Texaco Inc., White Plains, N.Y.

[21] Appl. No.: 515,748

[22] Filed: Jul. 21, 1983

[51] Int. Cl.³ .................. C07C 51/56; C07C 51/12
[52] U.S. Cl. .................................. 260/549; 562/519
[58] Field of Search ..................... 260/549; 562/519

[56] References Cited

U.S. PATENT DOCUMENTS

| | | | |
|---|---|---|---|
| 2,727,902 | 12/1955 | Reppe et al. | 260/546 |
| 2,730,546 | 1/1958 | Reppe et al. | 260/549 |
| 4,115,444 | 9/1978 | Rizkalla | 260/549 |
| 4,140,865 | 2/1979 | Fernholz et al. | 562/519 |
| 4,189,441 | 2/1980 | Braca et al. | 568/671 |
| 4,337,351 | 6/1982 | Larkins | 560/232 |

*Primary Examiner*—Natalie Trousof
*Assistant Examiner*—L. Hendriksen
*Attorney, Agent, or Firm*—Jack H. Park; Richard A. Morgan; Cynthia L. Kendrick

[57] ABSTRACT

A process for producing acetic anhydride is disclosed which comprises reacting methyl acetate with carbon monoxide at an elevated temperature and pressure in the presence of an iodine-free catalyst system wherein the catalyst consists of ruthenium compound, quaternary phosphonium salt and cobalt-compound. A further embodiment comprises recycling product acetic anhydride with methanol to produce acetic acid.

8 Claims, No Drawings

PROCESS FOR SELECTIVELY PREPARING ACETIC ANHYDRIDE BY CARBONYLATION OF METHYL ACETATE IN THE PRESENCE OF AN IODIDE-FREE CATALYST SYSTEM

FIELD OF THE INVENTION

This invention pertains to the production of acetic anhydride with high selectivity by carbonylation of methyl acetate in the presence of a novel iodide-free catalyst system at a temperature of at least 150° C. and at least 2000 psi.

BACKGROUND OF THE INVENTION

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drawbacks and disadvantages and the search for an improved process for the production of acetic anhydride has been a continuing one. Proposals for producing anhydrides by the action of carbon monoxide upon various reactants (carbonylation) have been described, for example, in Reppe et al. U.S. Pat. Nos. 2,729,561, 2,730,546 and 2,789,137. However, such prior proposals involving carbonylation reactions have required the use of very high pressures. More recently carbonylation at lower pressures has been proposed, but primarily as a route to the preparation of acetic acid. French Pat. No. 1,573,130, for example, describes the carbonylation of methanol and mixtures of methanol with methyl acetate in the presence of compounds of Group VIII noble metals such as iridium, platinum, palladium, osmium, and ruthenium and in the presence of bromine or iodine under more moderate pressures than those contemplated by Reppe et al. Similarly, South African Pat. No. 68/2174 produces acetic acid from the same reactants using a rhodium component with bromine or iodine. Schultz (U.S. Pat. Nos. 3,689,533 and 3,717,670) has disclosed a vapor phase process for acetic acid production employing various catalysts comprising a rhodium component dispersed on a carrier. None of these later carbonylation disclosures, however, refers to or contemplates the preparation of acetic anhydride or other carboxylic acid anhydrides, and they use the corrosive iodine promoter.

Improved processes for preparing carboxylic acid anhydrides, including acetic anhydride, have been disclosed by Colin Hewlett and Nabil Rizkalla. In these processes Group VIII metals are catalyst components.

In U.S. Pat. Nos. 4,002,677 and 4,002,678, Nagliri et al. use nickel-chromium catalysts at lower pressures than the art prior to produce carboxylic acid anhydrides. However, corrosive iodine promoters are again used.

Rhodium catalyst in combination with iodine promotor effected for acetic anhydride synthesis had also been disclosed in U.S. Pat. Nos. 4,251,458 and 4,284,586.

It is an object of this invention to selectively produce acetic anhydride via carbonylation of the ester derivative of methanol, methyl acetate, using a catalyst system which contains no corrosive iodine promoter required by catalysts of the prior art and which operates at lower pressures.

Further, it is an object of this invention to provide a process for recycling acetic anhydride produced, adding methanol with the recycled product and producing acetic acid.

SUMMARY OF THE INVENTION

These and other objects of this invention are achieved by a process comprising carbonylation of methyl acetate in the presence of a bimetallic iodide-free catalyst system comprising a ruthenium-containing compound, a quaternary phosphonium salt and a cobalt-containing compound at a temperature of between 150° C. and 350° C. and a pressure of 2000 psi to 7000 psi.

DETAILED DESCRIPTION OF THE INVENTION

In the broadest aspect of this invention, acetic anhydride is prepared from methyl acetate by contacting said reactant with carbon monoxide in the presence of a bimetallic iodide-free catalyst system comprising a ruthenium-containing compound, a cobalt-containing compound and a quaternary phosphonium salt at a temperature of at least 150° C. and a pressure of at least 2000 psi.

The disclosed catalyst provides an iodine-free system for methyl acetate carbonylation into acetic anhydride according to the equation:

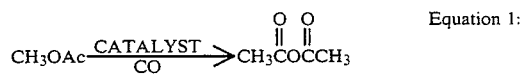

Equation 1:

In the narrower practice of this invention, acetic anhydride is produced by a process comprising reacting methyl acetate with carbon monoxide in the presence of a bimetallic iodide-free catalyst system comprising a ruthenium containing compound, a quaternary phosphonium salt and a cobalt-containing compound, heating resulting reaction mixture to a temperature of at least 150° C. and a pressure of at least 2000 psi with sufficient carbon monoxide to satisfy the stoichiometry of the desired anhydride product, until substantial formation of the desired anhydride has been achieved, and isolating said anhydrides contained therein.

In order to present the inventive concept in the greatest possible detail as to promote its understanding, the following supplementary disclosure is submitted.

A. Catalyst Composition

The catalyst precursors that are suitable in the practice of this invention essentially include a ruthenium component, a cobalt component, a quaternary phosphonium salt. A wide range of ruthenium catalyst compositions may be employed.

B. Ruthenium Catalyst Component

The ruthenium component to be used in conjunction with other catalyst components may be added in the form of a ruthenium oxide, as in the case of, for example, ruthenium(IV) dioxide hydrate, anhydrous ruthenium(IV) dioxide and ruthenium(VIII) tetraoxide, or as the salt of a mineral acid, as in the case of ruthenium(II) chloride, hydrate, ruthenium(III) bromide, anhydrous ruthenium(II) chloride and ruthenium nitrate. Alternatively, the ruthenium may be added as the salt of a suitable organic carboxylic acid. Here examples include ruthenium(III) acetate, ruthenium(III) propionate, ruthenium hexafluoroacetylacetonate, ruthenium(III) trifluoroacetate, ruthenium octanoate, ruthenium naphthenate, ruthenium valerate and ruthenium(III) acetylacetonate. This invention also contemplates the use of carbonyl or hydrocarbonyl derivatives such as triruthenium dodecacarbonyl, $H_2Ru_4(CO)_{13}$ and $H_4Ru_4(CO)_{12}$, and substituted carbonyl species such as the tricarbonylruthenium(II) dimer, $[Ru(CO)_3Cl_2]_2$.

Ruthenium compounds, especially useful in the soluble form of the catalyst include triruthenium dodecacarbonyl, ruthenium(III) chloride, ruthenium oxide hydrate and ruthenium(III) acetate. The preferred compound is ruthenium oxide hydrate.

Generally it is believed, without limiting the invention thereby, that the catalytically active ruthenium species of this invention, during the methyl acetate carbonylation is in the form of a coordination complex of ruthenium and the phosphonium salt that may or may not, contain carbon monoxide ligands. Other moieties may also be present as desired, and the ruthenium may be introduced into the reaction zone as a coordination complex of ruthenium containing hydride-ruthenium carbonyl.

C. Cobalt Catalyst Component

As previously pointed out in the process of this invention for producing acetic anhydride the reaction is conducted in the presence of a catalyst which includes a cobalt-containing compound. The cobalt-containing compound employed may be a cobalt carbonyl or a compound capable of forming a cobalt carbonyl under reaction conditions.

The cobalt-containing catalyst precursors may take many different forms. For instance, the cobalt may be added to the reaction mixture in an oxide form, as in the case of, for example, cobalt(II) oxide (CoO) or cobalt-(II, III) oxide ($Co_3O_4$). Alternatively, it may be added as the salt of a mineral acid, as in the case of cobalt(II) chloride ($CoCl_2$), cobalt(II) chloride hydrate ($CoCl_2.6H_2O$), cobalt(II) bromide ($CoBr_2$), and cobalt(II) nitrate hydrate ($Co(NO_3)_2.6H_2O$), etc., or as the salt of a suitable organic carboxylic acid, for example, cobalt(II) formate, cobalt(II) acetate, cobalt(II) propionate, cobalt naphthenate, cobalt acetylacetonate, etc. The cobalt may be added to the reaction zone as a carbonyl or hydrocarbonyl derivative. Here, suitable examples include dicobalt octacarbonyl ($Co_2(CO)_8$), cobalt hydrocarbonyl ($HCo(CO)_4$) and substituted carbonyl species such as the triphenylphosphine cobalt tricarbonyl dimer, etc.

Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(III) acetylacetonate, cobalt(II) acetate, cobalt(II) propionate, and especially preferred is dicobalt octacarbonyl.

D. Quaternary Phosphonium Salt

As previously pointed out in the process of this invention, the reaction includes a quaternary phosphonium salt.

Quaternary phosphonium salts suitable for use in this invention have the formula:

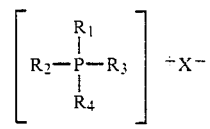

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding phosphonium acetates, nitrates, chromates, tetrafluoroborates and halides, such as bromides or chlorides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus atom through the aryl function.

Illustrative examples of suitable quaternary phosphonium salts include tetrabutylphosphonium bromide, heptyltriphenylphosphonium bromide, tetrabutylphosphonium chloride, tetrabutylphosphonium nitrate, tetrabutylphosphonium chromate, tetrabutylphosphonium tetrafluoroborate, tetrabutylphosphonium acetate and methyltriphenylphosphonium bromide.

The preferred quaternary salts are generally the phosphonium salts containing alkaryl groups which may comprise, for example, phenyl substituted with one or more alkyl substituents. The tetraalkyl salts work well and tetra-n-butylphosphonium salts such as the bromide, chloride, acetate and chromate salts are preferred. The bromide salt is most preferred for the practice of this invention because of its ready availability. Mixtures of these quaternary salts may also be employed if desired.

E. CATALYST COMPONENTS

The quantity of ruthenium catalyst employed in the instant invention is not critical and may vary over a wide range. In general, the carbonylation process is desirably conducted in the presence of a catalytically effective quantity of the active ruthenium species which gives the desired anhydride products in reasonable yields. The reaction proceeds when employing concentrations of ruthenium in solution of between 0.05 wt % and 20 wt %. This is the range normally employed, with the preferred range being 0.1 wt % to 5 wt %. Higher concentrations of ruthenium may be used to the extent of 20 wt %.

The quantity of cobalt-containing compound used in the process is not critical and may vary over a wide range. The reaction proceeds when employing concentrations of cobalt in solution of between 0.01 wt % and 20 wt %. This range is normally employed, with the preferred range being 0.1 wt % to 5 wt %. High concentrations of cobalt may be used to the extent of 20 wt %.

The quantity of substituted quaternary phosphonium salt used in the process for producing acetic anhydride may vary over a wide range also. The reaction proceeds when employing concentrations between 5 wt % and 50 wt %. The preferred range is between 15 wt % and 30 wt %. Higher concentrations may be used to the extent of 50 wt %.

In the production of acetic anhydride the proportions of ruthenium-containing compound to quaternary phosphonium salt to cobalt-containing compound may vary from 1.0:5.0:1.0 respectively to 1.0:20.0:4.0. Preferred weight percents for ruthenium range from 1% to 10%, for the quaternary phosphonium salt from 5% to 50% and for the cobalt-containing compound from 1% to 20%.

F. ADDITIONAL EMBODIMENTS

In the process for production of acetic anhydride of the instant invention, the catalyst has demonstrated a capability of producing acetic acid via recycling acetic anhydride along with methanol according to the equation:

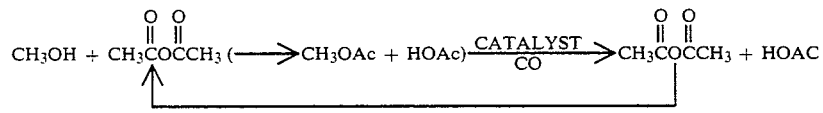

Equation 2:

G. OPERATION TEMPERATURE

The temperature range which can usefully be employed in these anhydride syntheses is a variable, dependent upon other experimental factors including the choice of ester reactant, the pressure, and the concentration and particular choice of catalyst, among other things. Again using ruthenium as the active metal, the range of operability is from about 100° to at least 400° C., when superatmospheric pressures of syngas are employed. A narrower range of 150°–350° C. represents the preferred temperature range when the major products are ester derivatives. Tables I–II are evidence of how the narrower range is derived.

H. PRESSURE

Superatmospheric pressures of 500 psi or greater lead to substantial yields of acetic anhydride by the process of this invention. A preferred operating range for solutions of ruthenium compound in combination with quaternary phosphonium salt and a cobalt compound is from 500 psi to 8000 psi, although pressures above 8000 psi also provide useful yields of desired anhydride. The preferred range is 4000–7500 psi. The pressures referred to here represent the total pressure generated by all the reactants, although they are substantially due to the carbon monoxide fraction in these examples. Table I and II are evidence of these narrower ranges.

I. GAS COMPOSITION

Insofar as can be determined, the best selectivities and yields of anhydride can be obtained within a reasonable reaction period by using a substantially carbon monoxide gaseous atmosphere. In all syntheses, the amount of carbon monoxide present in the reaction mixture is a variable, but sufficient carbon monoxide should be present to satisfy the stoichiometry of Equation 1 or 2.

Particularly in continuous operations, but also in batch experiments, the carbon monoxide may also be used in conjunction with up to 50% by volume of one or more other gases. These other gases may include one or more inert gases such as nitrogen, argon, neon and the like, or they may include gases that may, or may not, undergo reaction under CO carbonylation conditions such as carbon dioxide, hydrogen, hydrocarbons such as methane, ethane, propane and the like, ethers such as dimethyl ether, methylethyl ether and diethyl ether, alkanols such as methanol and acid esters such as methyl acetate.

J. PRODUCT DISTRIBUTION

As far as can be determined, without limiting the invention thereby, the ruthenium catalyzed, one-step carbonylation process disclosed herein leads to the formation of ester derivatives of these carboxylic acids. In the case where methyl acetate is the reactant the principal products are acetic anhydride and acetic acid. Minor by-products detected in the liquid product fraction include small amounts of water, ethyl acetate and dimethyl ether. Carbon dioxide, methane and dimethyl ether may be detected in the off-gas together with unreacted carbon monoxide.

K. IDENTIFICATION PROCEDURE

The products of carbonylation have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts by weight; all temperatures are in degrees centigrade and all pressures in pounds per square inch gauge (psi).

L. MODE OF OPERATION

The process of this invention can be conducted in a batch, semi-continuous or continuous fashion. The ruthenium compound, quaternary salt and cobalt compound catalyst may be introduced into the reaction zone batchwise, or may be continuously or intermittently introduced into such a zone during the course of the synthesis reaction. Operating conditions can be adjusted to optimize the formation of the desired acid product, and said material may be recovered by methods well known in the art, such as distillation, fractionation, extraction and the like.

In the process for producing acetic anhydride, a fraction rich in acetic anhydride can be recycled to the reaction zone with added methanol and acetic acid generated.

Generally, operating conditions can be adjusted to optimize the formation of any desired anhydride products, and said materials may be recovered by methods well known in the art, such as distillation, fractionation, extraction and the like. By-product esters, methyl and ethyl acetate, may then be recycled to the reaction zone, if desired, and additional anhydride and ester products generated by CO carbonylation.

Having described the inventive process in general terms, the following examples are submitted to supply specific and illustrative embodiments.

EXAMPLE I

Examples I through VIII illustrate the process of this invention for producing acetic anhydride by carbonylation of methyl acetate in the presence of a bimetallic catalyst.

In Example I a glass liner was charged with 0.19 g (1.0 mmole) of hydrated ruthenium(IV) dioxide, 3.4 g (10 mmoles) of tetra-n-butylphosphonium bromide, 0.34 g (1 mmole) of dicobalt octacarbonyl and 10 ml of methyl acetate. The glass liner was placed in a stainless steel reactor. The reactor was purged of air and pressured to 2000 psi with carbon monoxide then was heated to 220° C. while it was agitated by rocking. The pressure was brought up to 5690 psi and constant pressure was maintained by repressuring from a surge tank. The reaction was stopped after 18 hours and the reactor cooled to room temperature. An off-gas sample was taken and excess gas vented from the reactor following which 13.9 g of dark brown product was recovered. Analysis of the liquid product by glc showed the presence of: 28% MeOAc, 0% HOAc and 46% $(CH_3CO)_2O$. The methyl acetate conversion was calculated to be 72% and acetic anhydride selectivity was 64%. This example illustrates a process for producing acetic anhydride without using iodide promoter.

A typical off-gas sample showed the presence of 94% carbon monoxide, 0.7% methane and 3.6% carbon dioxide. The water content as determined by Karl Fischer titration was 0.02%.

EXAMPLE II

A glass liner was charged with 0.19 g (1.0 mmole) of hydrated ruthenium(IV) dioxide, 3.4 g (10.0 mmoles) of tetra-n-butylphosphonium bromide, 0.34 g (1 mmole) of dicobalt octacarbonyl, 5.0 g of methanol and 17.5 g of acetic anhydride. A small amount of sample was withdrawn and the mixture showed by glc analysis was 51% MeOAc, 39% HOAc and 10% $(CH_3CO)_2O$. The glass liner was placed in a stainless steel reactor. The reactor was purged of air and pressured to 3500 psi with carbon monoxide then was heated to 220° C. while it was agitated by rocking. The pressure reached 5350 psi after heating. No surge tank was used and the pressure dropped to 5200 psi during the reaction procedure. The reaction was stopped after 18 hours and the reactor cooled to room temperature. An off-gas sample was taken and excess gas vented from the reactor following which 25.6 g of dark brown product was recovered. Analysis of the liquid product by glc showed the presence of: 38% MeOAc, 39% HOAc and 22% $(CH_3CO)_2O$. The methyl acetate conversion was calculated to be 25% and acetic anhydride selectivity was 100%. An off-gas sample showed the presence of 96.9% carbon monoxide, 0.96% methane and 0.87% carbon monoxide. The water content was 0.02% by Karl Fischer analysis.

This example illustrates the production of acetic anhydride in the presence of acetic acid or a process producing acetic acid with addition of methanol to acetic anhydride.

COMPARATIVE EXAMPLE III

Example III was performed according to the procedure of Example I except no dicobalt octacarbonyl was used.

Here the catalyst minus the dicobalt octacarbonyl were used in the procedure of Example I. The pressure was brought up to 5530 psi and 220° C. The reaction was stopped after 18 hours and analysis of the liquid product by glc showed the presence of: 0.02% $H_2O$, 91% MeOAc, 0% HOAc and 0.7% $(CH_3CO)_2O$. These results demonstrate the importance of the cobalt-containing compound for producing acetic anhydride.

EXAMPLES IV AND V

In Examples IV and V the procedure of Example I was used and the catalyst system comprised $RuO_2$/n-$Bu_4PBr$/$Co_2(CO)_8$. The feedstock used was methanol and acetic anhydride. Product acetic anhydride was recycled with methanol. Pressures varied between 6000 psi and 7500 psi. The data demonstrate the various results.

It is noted that under both sets of conditions the percentage of acetic acid produced was 40% or greater. Data is set forth in Table I.

TABLE I

| EXAMPLE | (Catalyst) (mmole used) | Starting Materials | Reaction Conditions | $H_2O$ % | Product Distribution (wt %) | | |
|---|---|---|---|---|---|---|---|
| | | | | | MeOAc | HOAc | $(CH_3CO)_2O$ |
| IV | $RuO_2$/n-$Bu_4PBr$/Co(CO)$_8$ (1:10:1) | $CH_3OH$ 5.0 g $(CH_3CO)_2O$ 17.5 g | 6250 psi Co 220° C. 18 hrs. | 0.03 | 34 | 40 | 25 |
| V | $RuO_2$/n-$Bu_4PBr$/Co(CO)$_8$ (1:10:3) | " " | 7500 psi Co 220° C. 18 hrs. | — | 33 | 43 | 23.5 |

EXAMPLE VI

Example VI was performed according to the same procedures as Examples IV and V except the quaternary used was methyltriphenylphosphonium bromide, mmole ratio of catalyst was $RuO_2$/$CH_3Ph_3PBr$/$Co_2(CO)_8$ (1:10:3) respectively and the pressure was 7180 psi. Data showing resulting product distribution are shown below:

| | |
|---|---|
| $H_2O$ %: | — |
| MeOAc: | 28.6 |
| HOAc: | 43 |
| $(CH_3CO)_2O$: | 27.6 |

EXAMPLES VII–VIII

Examples VII and VIII were performed according to procedure of Example I. Results are shown in Table II.

TABLE II

| EXAMPLE | (Catalyst) (mmole used) | Starting Materials | Reaction Conditions | $H_2O$ % | Product Distribution (wt %) | | |
|---|---|---|---|---|---|---|---|
| | | | | | MeOAc | HOAc | $(CH_3CO)_2O$ |
| VII | $RuO_2$/n-$Bu_4PBr$/Co(CO)$_8$ (1:10:1) | $CH_3OAc$ 9.3 g $(CH_3CO)_2O$ 10 g | 6600 psi Co 220° C. 18 hrs. | — | 29 | 20 | 45 |

TABLE II-continued

| EXAMPLE | (Catalyst) (mmole used) | Starting Materials | Reaction Conditions | H₂O % | Product Distribution (wt %) | | |
|---|---|---|---|---|---|---|---|
| | | | | | MeOAc | HOAc | (CH₃CO)₂O |
| VIII | RuO$_2$/n-Bu$_4$PBr/Co(CO)$_8$ (1:10:3) | CH$_3$OAc 10 ml (CH$_3$CO)$_2$O 10 ml) | 6800 psi Co 250° C. 18 hrs. | — | 45 | 26 | 20 |

What is claimed is:

1. A process for the production of acetic anhydride which comprises reacting methyl acetate with carbon monoxide in the presence of an iodide-free bimetallic catalyst system comprising a ruthenium-containing compound from the group consisting of one or more oxides of ruthenium, ruthenium complexes with carbonyl-containing ligands and ruthenium carbonyl or hydrocarbonyl derivatives, a quaternary phosphonium salt and a cobalt-containing compound at a temperature of between 150° C. and 350° C. and a pressure of between 2000 psi and 7000 psi.

2. The process of claim 1 wherein the ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetyl acetonate and triruthenium dodecacarbonyl.

3. The process of claim 1 wherein the quaternary phosphonium salt is selected from the group consisting of tetrabutylphosphonium bromide, tetrabutylphosphonium chloride, tetrabutylphosphonium acetate and tetrabutylphosphonium chromate.

4. The process of claim 3 wherein the quaternary phosphonium salt is tetra-n-butylphosphonium bromide.

5. The process of claim 1 wherein the cobalt-containing compound is selected from the group consisting of one or more oxides of cobalt, cobalt salts of a mineral acid, cobalt carbonyls or hydrocarbonyl derivatives.

6. The process of claim 1 wherein the cobalt-containing compound is dicobalt octacarbonyl.

7. The process of claim 1 wherein the mmole ratio of ruthenium-containing compound to quaternary phosphonium salt to cobalt-containing compound is from 1.0:5.0:1.0 to 1.0:20.0:4.0.

8. The process of claim 1 further comprising recycling part of said product acetic anhydride with methanol in the presence of said catalyst system to form acetic acid.

* * * * *